United States Patent [19]

Böttcher et al.

[11] Patent Number: 5,418,237

[45] Date of Patent: May 23, 1995

[54] INDOLE DERIVATIVES

[75] Inventors: Henning Böttcher; Hartmut Greiner, both of Darmstadt; Christoph Seyfried, Jugenheim; Gerd Bartoszyk, Darmstadt, all of Germany

[73] Assignee: Merck Patent Gesellschaft mit Beschrankter Haftung, Darmstadt, Germany

[21] Appl. No.: 262,256

[22] Filed: Jun. 13, 1994

Related U.S. Application Data

[63] Continuation of Ser. No. 824,138, Jan. 22, 1992, abandoned.

[30] Foreign Application Priority Data

Jan. 22, 1991 [DE] Germany .................. 41 01 686.6

[51] Int. Cl.$^6$ ............................................. C07D 403/00
[52] U.S. Cl. ................................................. 514/253
[58] Field of Search ............... 544/357, 360, 364, 121, 544/373; 514/253, 235.8

[56] References Cited

U.S. PATENT DOCUMENTS

| | | | |
|---|---|---|---|
| 3,466,287 | 9/1969 | Archer | 544/373 |
| 3,468,882 | 9/1969 | Laskowski | 544/373 |
| 3,562,278 | 2/1971 | Archer | 544/373 |
| 3,639,414 | 2/1972 | Archer | 544/373 |
| 4,252,803 | 2/1981 | Webb | 544/373 |
| 4,272,533 | 6/1981 | Gadient et al. | 544/373 |
| 4,710,500 | 12/1987 | Perregaard | 544/373 |
| 4,785,016 | 11/1988 | Evans et al. | 544/373 |
| 5,002,948 | 3/1991 | Perregaard et al. | 544/373 |
| 5,010,079 | 4/1991 | Manoury et al. | 544/373 |
| 5,106,850 | 4/1992 | Bütcher et al. | 544/368 |

FOREIGN PATENT DOCUMENTS

| | | | |
|---|---|---|---|
| 1075156 | 7/1967 | United Kingdom | 544/373 |
| 1075176 | 7/1967 | United Kingdom . | |
| 1116196 | 6/1968 | United Kingdom | 544/373 |
| 1189064 | 4/1970 | United Kingdom . | |
| 1326833 | 8/1973 | United Kingdom . | |

OTHER PUBLICATIONS

Ho et al., "Inhibitors of Hydroxyindole-O-methyltransferase: Indole-alkylpiperazines," Journal of Pharmaceutical Sciences, vol. 62, No. 3, pp. 508-509 (Mar. 1973).
CA 78:58465g (1973).

*Primary Examiner*—Cecilia Tsang
*Attorney, Agent, or Firm*—Millen, White, Zelano, & Branigan

[57] ABSTRACT

Indole derivatives of formula I

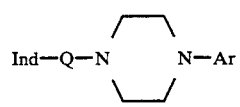

wherein Ind, Q and Ar are as defined herein, and their salts, are active on the central nervous system.

13 Claims, No Drawings

INDOLE DERIVATIVES

This application is a continuation of application Ser. No. 07/824,138, filed Jan. 22, 1922, now abandoned.

SUMMARY OF THE INVENTION

The invention relates to novel indole derivatives of formula I

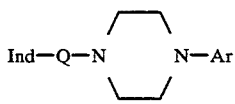

wherein
- Ind is an indol-3-yl radical substituted by CN, CO—$R^1$, $C_nH_{2n}$—$R^1$, Hal, OH, OA, O—$C_nH_{2n}$—$COR^1$, CO—$NR^3R^4$ or $NHR^2$,
- $R^1$ is OH, OA, $NH_2$, NHA, $NA_2$, $NHC_nH_{2n}NA_2$, $NHC_nH_{2n}$Het, $NHC_nH_{2n}$OA, or O—CO—A,
- $R^2$ is H, CO—A, CO—Ar, CO—$NH_2$, CO—NHA, CO—$NA_2$ or $SO_2$—A,
- $R^3$ and $R^4$ together are an alkylene group having 3–7 C atoms, which can be interrupted by O or $NR^5$ and/or substituted by O, $NA_2$, NHCOA, COOA, $CONH_2$, Ar or Het, and/or can contain an additional double bond,
- $R^5$ is H, A, Ar, Het, Ar—CO, COOA, $CH_2CONH_2$, $CH_2$CONHA, $CH_2CONA_2$ or CHO,
- Q is $C_nH_{2n}$,
- n is 1, 2, 3, 4, 5 or 6,
- A is alkyl having 1–6 C atoms,
- Ar is a phenyl radical which is unsubstituted or mono-, di- or trisubstituted by A, F, Cl, Br, I, CN, OH, OA and/or $CF_3$ or substituted by a methylenedioxy group,
- Het is a saturated or unsaturated 5-membered or 6-membered heterocyclic radical having 1–4N, O and/or S atoms, which can be fused with a benzene ring and/or mono-substituted or disubstituted by A, Ar, —O(CH$_2$)$_2$O—, carbonyloxygen or a further Het radical, and
- Hal is F, Cl, Br or I and to their salts.

An object of the invention is to provide novel compounds capable of being used for the preparation of drugs.

Upon further study of the specification and appended claims, further objects and advantages of this invention will become apparent to those skilled in the art.

It has been found that the compounds of formula I and their biocompatible acid addition salts possess valuable pharmacological properties. Thus, in particular, they are active on the central nervous system, especially as serotonin agonists and antagonists. They inhibit the binding of tritiated serotonin ligands to hippocampal receptors (Cossery et al., European J. Pharmacol. 140 (1987), 143–155). They also modify the accumulation of DOPA in the corpus striatum and the accumulation of 5-HTP in the nuclei raphes (Seyfried et al., European J. Pharmacol. 160 (1989), 31–41). They also have analgesic and hypotensive effects; thus, in catheterized, conscious, spontaneously hypertensive rats (strain: SHR/Okamoto/NIH-MO-CHB-Kisslegg; methods q.v. Weeks and Jones, Proc. Soc. Exptl. Biol. Med. 104 (1960), 646–648), the directly measured blood pressure is lowered after oral administration of the compounds. They are also useful for prophylaxis and control of the sequelae of cerebral infarction (Apoplexia cerebri) such as stroke and cerebral ischaemia.

Compounds of formula I and their biocompatible acid addition salts can therefore be used as active ingredients for anxiolytics, antidepressants, neuroleptics, and/or antihypertensives, and also as intermediates for the preparation of other pharmaceutical active ingredients.

The invention relates to the indole derivatives of formula I and to their biocompatible acid addition salts.

The radical A is alkyl having 1, 2, 3, 4, 5 or 6 C atoms, especially 1 or 2 C atoms, preferably methyl and also ethyl, n-propyl, isopropyl, n-butyl, isobutyl, sec-butyl or tert-butyl. OA is preferably methoxy and also ethoxy, n-propoxy, isopropoxy, n-butoxy, isobutoxy, sec-butoxy or tert-butoxy. NHA is preferably methylamino and also ethylamino, n-propylamino, isopropylamino, n-butylamino, isobutylamino, sec-butylamino or tert-butylamino. $NA_2$ is preferably dimethylamino and also N-ethyl-N-methylamino, diethylamino, di-n-propylamino, diisopropylamino or di-n-butylamino.

Analogously, CO—NHA is preferably N-methylcarbamoyl or N-ethylcarbamoyl; CO—$NA_2$ is preferably N,N-dimethylcarbamoyl or N, N-diethylcarbamoyl and $SO_2$—A is preferably methylsulphonyl or ethylsulphonyl.

The radical Ar is preferably unsubstituted phenyl but can also be mono-, di- or trisubstituted phenyl. If phenyl is di- or trisubstituted, it is possible for the substituents to be identical or different. Preferred substituents on the phenyl group are F, Cl, methoxy, CN, $CF_3$, $NHCOCH_3$ or methyl. Where the phenyl radicals are substituted, the substituents are in the ortho, meta and-/or paraposition, di- and trisubstituted phenyl radicals preferably being ortho- and para-substituted. Specifically, Ar is preferably phenyl, o-, m- or p-trifluoromethylphenyl, o-, m-, or p-methoxyphenyl, o-, m- or p-fluorophenyl, o-, m- or p-methylphenyl, o-, m- or p-cyanophenyl or 2,4-dimethoxyphenyl, but also o-, m- or p-ethoxyphenyl, o-, m- or p-bromophenyl, 2,3-, 2,5-, 2,6-, 3,4- or 3,5-dimethoxyphenyl, 2,3- or 3,4-methylenedioxyphenyl or 3,5-dichloro-4-methoxy-phenyl.

Het is preferably 1-pyrrolidinyl, 1-piperidinyl, 1,2-dihydro-1-pyridinyl, 1,2,3,6-tetrahydro-1-pyridinyl, 4-morpholinyl or 1-piperazinyl, and also 2,6-, 2,5-, 3,5- or 3,6-dimethyl-4-morpholinyl.

Het is also preferably furan-2-yl or furan-3-yl, thien-2-yl or thien-3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or -5-yl, thiazol-2 -, -4- or -5-yl, isothiazol-3-, -4- or -5-yl, pyrid-2-, -3- or -4-yl or pyrimidin-2-, -4-, -5- or -6-yl, other preferred meanings being 1,2,3-triazol-1-, -4- or -5-yl, 1,2,4-triazol-1-, -3- or -5-yl, tetrazol-1- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3-or -5-yl, 1,2,3-thiadiazol-4- or -5-yl, 2H-thiopyran-2-, -3-, -4-, -5- or -6-yl, 4H-thiopyran-2-, -3- or -4-yl, pyridazin-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4-, -5-, -6- or -7-yl, benzisoxazol-3-, -4-, -5-, -6- or -7-yl, benzthiazol-2-, -4-, -5-, -6- or -7-yl, benzisothiazol-2-, -4-, -5-, -6- or -7-yl, benz-2,1,3-oxadiazol-4-, -5-, -6- or -7-yl, quinol-2-, -3-, -4-, -5-, -6-, -7- or -8-yl, isoquinol-1-, -3-, -4-, -5-, -6-, -7- or -8-yl, carbazol-1-, -2-, -3-, -4- or -9-yl, acridin-1-, -2-, -3-, -4-, -5-, -6-, -7-, -8- or -9-yl, cinnol-3-, -4-, -5-, -6-, -7- or -8-yl or quinazol-2-, -4-, -5-, -6-, -7- or -8-yl. Further heterocyclic radicals which can be partially or completely hydrogenated can also be, e.g., 2,3-dihydrofuran-2-, -3-, -4- or -5-yl, 2,5-dihydrofuran-2-, -3-, -4- or -5-yl, tetrahydrofuran-2- or -3-yl, tetrahydrothien-2- or -3-yl, 2,3-dihydropyrrol-1-, -2-, -3-, -4- or -5-yl, 2,5-dihydropyrrol-1-, -2-, -3-, -4- or -5-yl, pyrrolidin-1-, -2- or -3-yl, tetrahydroimidazol-1-, -2- or -4-yl, 2,3-dihydropyrazol-1-, -2-, -3-, -4- or -5-yl, tetrahydropyrazol-1-, -3- or -4-yl, 1,4-dihydropyrid-1-, -2-, -3- or -4-yl, 1,2,3,4-tetrahydropyrid-1-, -2-, -3-, -4-, -5- or -6-yl, 1,2,3,6-tetrahydropyrid-1-, -2-, -3-, -4-, -5- or -6-yl, piperidin-1-, -2-, -3- or -4-yl, morpholin-2- or -3-yl, tetrahydropyran-2-, -3- or -4-yl, 1,4-dioxanyl, 1,3-dioxan-2-, -4- or -5-yl, hexahydropyridazin-1-, - 3 - or - 4 -yl, hexahydropyrimidin-1-, -2-, -4- or -5-yl, piperazin-2- or -3-yl, 1,2,3,4-tetrahydroquinol- 1-, -2-, -3-, -4-, -5-, -6-, -7- or -8-yl or 1,2,3,4 -tetrahydroisoquinol- 1-, -2-, -3-, -4-, -5-, -6-, -7- or -8-yl.

The heterocyclic radicals can also be substituted as indicated. Het can also be, e.g., 4- or 5-methylthiazol -2-yl, 4-, 5- or 6-methylpyrimidin-2-yl, 4,5-dimethylthiazol-2-yl, 3-, 4- or 5-methylfuran-2-yl, 2-, 4- or 5-methylfuran-3-yl, 2,4-dimethylfuran-3-yl, 3-, 4- or 5-methylthien-2-yl, 2-, 4- or 5-methylthien-3-yl or 3-methyl-5-tert-butylthien-2-yl and in addition also e.g. 2-, 3- or 4-phenyl- 1-piperidinyl, 2-, 3-, 5- or 6-phenyl-1-morpholinyl.

The radical Ind is an indol-3-yl radical monosubstituted by one of the radicals indicated. It is preferably substituted in the 5-position or else in the 4-, 6- or 7-position. Substitution in the 1- or 2-position is a further possibility. Preferred substituents on the indol-3-yl radical are $CO_2CH_3$, $CO_2H$, CN, $CONH_2$, $CH_2OH$, $H_2N—CO—NH$, $CH_3—SO_2—NH$ and $CH_3—CO—NH$, but also OH, methoxy, ethoxy, $NH_2$, NHA or $NA_2$, A preferably being methyl or ethyl.

The parameter n can be 1, 2, 3, 4, 5 or 6, preferably 1, 2 or 4.

The radical Q is preferably —$(CH_2)_4$—, furthermore —$CH_2$—, —$(CH_2)_2$ or —$(CH_2)_3$—.

$R^1$ is preferably OH, methoxy, CN or $NH_2$, furthermore preferably ethoxy, $NH—CH_3$ or $N(CH_3)_2$.

$R^2$ is preferably $CO—CH_3$, $CO—NH_2$ or $SO_2—CH_3$, furthermore $CO—NH—CH_3$ or $CO—N(CH_3)_2$, but also CO-phenyl or $SO_2$-phenyl or $SO_2$-tolyl.

$R^3$ and $R^4$ always occur in the form of —$NR^3R^4$. The group —$NR^3R^4$ is preferably 1-piperidinyl, 4-$R^5$-piperidinyl, 1,2-dihydro-1-pyridinyl, 1,2,3,6-tetrahydro-1-pyridinyl, 4-morpholinyl, 1-piperazinyl, 3-keto-1-piperazinyl, 4-$R^5$-1-piperazinyl or 1-pyrrolidino, and also 2,6-, 2,5- or 3,5-dimethyl-4-morpholinyl.

$R^5$ is preferably H, A, Ar, 2-pyrimidinyl, 4- or 5-methyl-2thiazole, Ar—CO, COOA, $CH_2CONHA$ or CHO.

Accordingly, the invention relates particularly to those compounds of formula I in which at least one of said radicals has one of the meanings indicated above, especially one of the preferred meanings indicated above. Some preferred groups of compounds can be expressed by the following partial formulae Ia to Ii, which correspond to formula I and in which the radicals and parameters not described in greater detail are as defined for formula I, but in which:

in Ia, Ind is an indol-3-yl radical substituted in the 5-position by CO—$R^1$;

in Ib, Ind is an indol-3-yl radical substituted in the 5-position by $NHR^2$;

in Ic, Ind is an indol-3-yl radical substituted in the 5-position by COOH;

in Id, Ind is an indol-3-yl radical substituted in the 5-position by $COOCH_3$;

in Ie, Ind is an lndol-3-yl radical substituted in the 5-position by $CONH_2$;

in If, Ind is an indol-3-yl radical substituted in the 5-position by CN;

in Ig, Ind is an indol-3-yl radical substituted in the 5-position by $CH_2OH$;

in Ih, Ind is an indol-3-yl radial substituted in the 5-position by NH—CO—$NH_2$; and in Ii, Ind is an lndol-3-yl radical substituted in the 5-position by NH—$SO—CH_3$.

Especially preferred compounds are those of partial formulae Ik and Iak to Iik, which correspond to partial formulae I and Ia to Ii, but in which additionally:

Q is —$(CH_2)_4$—. 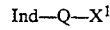

Other especially preferred compounds are those of partial formulae Il and Ial to Iil, which correspond to partial formulae I and Ia to Ii, but in which additionally:

Ar is phenyl, o-, m- or p-methoxyphenyl, 2,4 -dimethoxyphenyl, o-, m- or p-fluorophenyl or else o-, m- or p-cyanophenyl.

The invention further relates to a process for the preparation of indole derivatives of formula I and their salts, characterized in that a compound of formula II Ind—Q—$X^1$      II wherein $X^1$ is X or $NH_2$, X is Cl, Br, I, OH or an OH group functionally modified to form a reactive group, and Ind and Q are as defined, is reacted with a compound of formula III $X^2$—$CH_2$—$CH_2$—NAr—$CH_2$—$CH_2X^3$      III

wherein $X^2$ and $X^3$ can be identical or different and are each X if $X^1$=$NH_2$ or are together NH in other cases, and Ar is as defined, or in that a compound of formula IV Ind—Q—N($CH_2$—$CH_2$—X)$_2$      IV

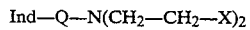

wherein

X, Q and Ind are as defined, is reacted with a compound of formula V

Ar—$NH_2$      V

wherein

Ar is as defined, or in that a compound which has formula I except that one or more hydrogen atoms have been replaced by one or more reducible groups and/or one or more additional C—C and/or C—N bonds are treated with a reducing agent, or in that a compound which has formula I except that one or more hydrogen atoms have been replaced by one or more solvolyzable groups is treated with a solvolyzing agent, and/or in that an OA group is optionally cleaved to form an OH group, and/or an Ind group and/or an Ar group is converted into another Ind and/or Ar group, and/or in that a resulting base or acid of formula I is converted into one of its salts by treatment with an acid or base.

The compounds of formula I are otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York; German Offenlegungsschrift 33 42 632 ), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compounds of formula I.

In the indole derivatives of formula II, $X^1$ is preferably X; accordingly, in the compounds of formula III, $X^2$ and $X^3$ are together preferably NH. The radical X is preferably Cl or Br, but it can also be I, OH or an OH group functionally modified to form a reactive group, especially alkylsulphonyloxy having 1-6 C atoms (e.g., methanesulphonyloxy) or arylsulphonyloxy having 6-10 C atoms ( e.g., benzenesulphonyloxy, p-toluenesulphonyloxy, naphthalene-1- or -2-sulphonyloxy).

Accordingly, the indole derivatives of formula I can be obtained especially by reacting compounds of the formula Ind—Q—Cl or Ind—Q—Br with piperazine derivatives of formula III in which $X^2$ and $X^3$ together are an NH group (designated as IIIa hereafter).

Some of the compounds of formulae II and, in particular, III are known; the unknown compounds of formulae II and III can easily be prepared analogously to the known compounds.

Primary alcohols of the formula Ind—Q—OH can be obtained, e.g., by reducing the appropriate carboxylic acids or their esters. Treatment with thionyl chloride, hydrogen bromide, phosphorus tribromide or similar halogen compounds yields the corresponding halides of the formula Ind—Q—Hal. The corresponding sulphonyloxy compounds can be obtained from the alcohols Ind—Q—OH by reaction with the appropriate sulphonyl chlorides.

The iodine compounds of the formula Ind—Q—I can be obtained, e.g., by reacting potassium iodide with the appropriate p-toluenesulphonic acid esters. The amines of the formula Ind—Q—NH$_2$ can be prepared, e.g., from the halides with potassium phthalimide or by reducing the appropriate nitriles.

Most of the piperazine derivatives IIIa are known and can be obtained, e. g., by reacting di-(2-chloroethyl )-amine with aniline or a corresponding aniline derivative substituted on the phenyl ring. Compounds of formula III ($X^2$ and $X^3$=X in each case ) can be prepared, e.g., by reducing diesters of the formula alkylOOC—CH$_2$—NAr—CH$_2$—COO—alkyl to give compounds of the formula HO—CH$_2$—CH$_2$—NAr—CH$_2$—CH$_2$OH (III, $X^2$=$X^3$=OH), this being followed, if desired, by reaction with SOCl$_2$ or PBr$_3$.

The reaction of the compounds II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons such as benzene, toluene or xylene; ketones such as acetone or butanone; alcohol s such as methanol, ethanol, isopropanol or n-butanol; ethers such as tetrahydrofuran (THF) or dioxane; amides such as dimethylformamide (DMF) or N-methylpyrrolidone; or nitriles such as acetonitrile, or else, if desired, mixtures of these solvents with one another or mixtures with water. It can be favorable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of the amine component Ind—Q—NH$_2$ or of the piperazine derivative of formula IIIa. The reaction time is between a few minutes and 14 days, depending on the conditions used, and the reaction temperature is between about 0° and 150°, normally between 20° and 130°.

It is also possible to obtain a compound of formula I by reacting a compound of formula Ind—Q—N(CH$_2$—CH$_2$—X)$_2$ (IV) with a compound of formula Ar—NH$_2$ (V).

Some of the compounds of formulae IV and, in particular, V are known; the unknown compounds can easily be prepared analogously to the known compounds. Thus, compounds o f formula IV can easily be prepared by reaction of Ind—Q—NH$_2$ with 1,2-dihaloethane, halogen preferably representing chlorine or bromine. It is also possible to obtain compounds of type IV by reaction of Ind—Q—Cl, Ind—Q—Br or Ind—Q—I with secondary amines of formula HN(CH$_2$—CH$_2$X)$_2$.

The primary amines of formula V can be prepared starting from aniline by means of the diverse possibilities of electrophilic substitution of aromatic compounds known per so. It is also possible to convert appropriately substituted nitro compounds into the amines of formula V by reduction.

The reaction of compounds IV and V proceeds according to methods which are known from the literature for the alkylation of amines. The components can be melted with one another directly, without the presence of a solvent, if appropriate in a closed tube or in an autoclave, at normal pressure or at elevated pressure, an inert gas such as, e.g., N$_2$ being added to increase the pressure. However, it is also possible to react the compounds in the presence of an inert solvent. Suitable solvents are those mentioned previously for the reaction of II with III. The addition of an acid-binding agent to the reaction mixture can also have a favorable effect. The same bases are suitable as those previously described for the reaction of compounds II and III.

Depending on the reaction conditions chosen, the optimum reaction time is between a few minutes and 14 days, and the reaction temperature is between about 0° and 150°, usually between 20° and 130°.

A compound of formula I can also be obtained by treating a precursor, in which hydrogen atoms have been replaced by one or more reducible groups and/or one or more additional C—C and/or C—N bonds, with a reducing agent, preferably at temperatures of between −80° and 250°, in the presence of at least one inert solvent.

Reducible groups ( groups replaceable by hydrogen) are, in particular, oxygen in a carbonyl group, hydroxyl, arylsulphonyloxy ( e.g., p-toluenesulphonyloxy), N-benzenesulphonyl, N-benzyl or O-benzyl.

In principle, compounds containing only one of the above-mentioned groups or additional bonds, or compounds containing two or more of the above-mentioned groups or additional bonds adjacent to one another, can be converted into a compound of formula I by reduction, it being possible simultaneously to reduce substituents in the Ind group which are present in the starting compound. This is preferably carried out using nascent hydrogen or complex metal hydrides or by means of a Wolff-Kishner reduction or the reductions with hydrogen gas under transition metal catalysis.

Preferred starting materials for the reduction have formula VI

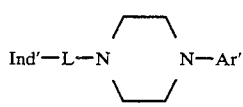
                             VI wherein
Ind' is an Ind radical which can additionally be substituted in the 1-position by an arylsulphonyl group or a benzyl group,
L is Q or a chain which corresponds to the radical Q except that one or more —$CH_2$— groups have been replaced by —CO— and/or one or more hydrogen atoms have been replaced by Cl, Br, F, SH, or OH groups,
Ar' is a phenyl group which is unsubstituted, monosubstituted, di- or trisubstituted by A, F, Cl, Br, I, CN, OA, OH, $CF_3$, NHCOA and/or O-benzyl or substituted by a methylenedioxy group,
but wherein the following meanings cannot apply simultaneously: Ind'=Ind, L=Q and Ar'=Ar.

In the compounds of formula VI, L is preferably —CO—$(C_2)_{n-2}$—CO— [specifically —COCO—, —$COCH_2CO$—, —CO—$(CH_2)_2$—CO—, —CO—$(CH_2)_3$—CO—], —$(CH_2)_{n-1}$—CO—[specifically —$CH_2$—CO—, —$CH_2CH_2$—CO—, —$CH_2$)$_3$—CO— or —$(CH_2)_4$—CO—], further examples being —CO—$CH_2CH_2$—, —CO—$(CH_3)_3$—, —$CH_2$—CO—$CH_2CH_2$—, —$CH_2CH_2$—CO—$CH_2$—, —CO—$(CH_2)_4$—, —$CH_2$—CO—$(CH_2)_3$—, —$CH_2CH_2$—CO—$CH_2CH_2$— or —$(CH_2)_3$—CO—$CH_2$—.

Compounds of formula VI can be prepared, e.g., by reacting 4-Ar'-piperazine with a compound of formula VII

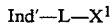                             VII wherein
Ar', Ind', L and $X^1$ are as defined above,
under the conditions indicated above for the reaction of II with III.

If nascent hydrogen is used as the reducing agent, this can be produced, e.g., by treating metals with weak acids or with bases. Thus it is possible, e.g., to use a mixture of zinc with an alkali metal hydroxide solution or a mixture of iron with acetic acid. It is also appropriate to use sodium or another alkali metal in an alcohol such as ethanol, isopropanol, butanol, amyl or isoamyl alcohol or phenol. It Is also possible to use an aluminium-nickel alloy in aqueous-alkaline solution, ethanol being added if necessary. Sodium amalgam or aluminium amalgam in aqueous-alcoholic or aqueous solution is also suitable for producing the nascent hydrogen. The reaction can also be carried out in the heterogeneous phase, in which case it is convenient to use an aqueous phase and a benzene or toluene phase.

Other reducing agents which can be used to particular advantage are complex metal hydrides such as $LiAlH_4$, $NaBH_4$, diisobutylaluminium hydride or $NaAl(OCH_2CH_2OCH_2)_2H_2$, and diborane, catalysts such as $BF_3$, $AlCl_3$ or LiBr being added if desired. Solvents which are suitable for this purpose are, in particular, ethers such as diethyl ether, di-n-butyl ether, THF, dioxane, diglyme or 1,2-dimethoxyethane, and hydrocarbons such as benzene. Solvents which are suitable for a reduction with $NaBH_4$ are primarily alcohols such as methanol or ethanol, as well as water and aqueous alcohols. Reduction by these methods is preferably carried out at temperatures of between −80° and +150°, especially of between about 0° and about 100°.

The reduction of —CO groups in acid amides (e.g., those of formula VI in which L is a —$(CH_2)_{n-1}$—CO group) to $CH_2$ groups can be carried out to particular advantage with $LIAlH_4$ in THF at temperatures of between about 0° and 66°. Arylsulphonyl protecting groups located in the 1-position of the indole ring can be simultaneously eliminated by reduction. N-Benzyl groups can be eliminated by reduction with sodium in liquid ammonia.

It is also possible to reduce one or more carbonyl groups to $CH_2$ groups according to the Wolff-Kishner method, e.g., by treatment with anhydrous hydrazine in absolute ethanol, under pressure, at temperatures of between about 150° and 250°. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 3–4 hours. The water is then distilled off and the hydrazone formed is decomposed at temperatures of up to about 200°. The Wolff-Kishner reduction can also be carried out with hydrazine in dimethyl sulphoxide at room temperature.

Moreover, it is possible to carry out certain reductions by using Ha gas under the catalytic action of transition metals, such as, e.g., Raney Ni or Pd. In this way, e.g., Cl, Br, I, SH or, in certain cases, even OH groups can be replaced by hydrogen. Nitro groups can also be converted into $NH_2$ groups by catalytic hydrogenation with $Pd/H_2$ in methanol.

Compounds which have formula I except that one or more H atoms have been replaced by one or more solvolyzable groups can be solvolyzed, especially hydrolyzed, to give the compounds of formula I.

The starting materials for the solvolysis can be obtained for example by reacting IIIa with compounds which have formula II ($X^1$=X) except that one or more H atoms have been replaced by one or more solvolyzable groups. Thus, in particular, 1-acylindole derivatives (which have formula I except that, in the 1-position of the Ind radical, they contain an acyl group, preferably an alkanoyl, alkylsulphonyl or arylsulphonyl group having up to 10 C atoms in each case, such as methanesulphonyl, benzenesulphonyl or p-toluenesulphonyl) can be hydrolyzed to give the corresponding indole derivatives unsubstituted in the 1-position of the indole ring, e.g., in an acidic or, preferably, neutral or alkaline medium at temperatures of between 0° and 200°. Sodium, potassium or calcium hydroxide, sodium or potassium carbonate, or ammonia, is conveniently used as the base. The chosen solvents are preferably water; lower alcohols such as methanol or ethanol; ethers such as THF or dioxane; sulphones such as tetramethylene sulphone; or mixtures thereof, especially mixtures containing water. Hydrolysis can also be carried out simply by treatment with water alone, especially at the boiling point.

A compound of formula I can furthermore be converted to another compound of formula I by methods known per se.

Compounds of formula I in which Ind is an indol-3-yl radical substituted by CO—$R^1$ can be obtained by derivatizing appropriate carboxyindol-3-yl compounds. It is possible, e.g., to esterify the acids or their reactive derivatives, such as, e.g., their acid halides or anhydrides, with appropriate alcohols or alcoholates, using the methodology known per se or one of the numerous variants. It is also possible to amidate acids, acid halides, anhydrides or esters with primary or secondary, aliphatic or cyclic amines. It is preferred to react the free carboxylic acid with the amine under the conditions of a peptide synthesis. This reaction 18 preferably carried out in the presence of a dehydrating agent, e.g., a carbodiimide such as dicyclohexylcarbodiimide or else N-(3-dimethylaminopropyl )-N-ethylcarbodiimide, or propanephosphonic anhydride (q.v. Angew. Chem. 92, 129 (1980)), diphenylphosphoryl azide or 2-ethoxy-N-ethoxycarbonyl-1,2-dihydroquinoline, in an inert solvent, e.g., a halogenated hydrocarbon such as methylene chloride, an ether such as THF or dioxane, an amide such as DMF or dimethylacetamide, or a nitrile such as acetonitrile, at temperatures of between about −10 and 40, preferably of between 0° and 30°. Instead of the acid or amide, it is also possible to use reactive derivatives of these substances in the reaction, e.g., those in which reactive groups are blocked by protecting groups in an intermediate step. The acids can also be used in the form of their activated esters, which are conveniently formed in situ, e.g., by the addition of 1-hydroxybenztriazole or N-hydroxysuccinimide.

Furthermore, cyano-substituted indol-3-yl radicals can be hydrolyzed to give carboxy-indol-3-yl or carbamido-indol-3-yl radicals.

Compounds of formula I can also be converted into other derivatives of formula I by transformations at the radical Ar.

Ethers of formula I in which the radical Ar is mono- or disubstituted by O-alkyl can be cleaved, the corresponding hydroxy derivatives being formed. It is possible, e.g., to cleave the ethers by treatment with dimethyl sulphide-boron tribromide complex, for example in toluene, ethers such as THF or dimethyl sulphoxide, or by melting with pyridine or aniline hydrohalides, preferably pyridine hydrochloride, at about 150°–250°.

If side reactions in the indole system are to be excluded, the radicals Ar can be chlorinated, brominated or alkylated under the conditions of the Friedel-Crafts reactions, by reacting the appropriate halogen or alkyl chloride or alkyl bromide under the catalysis of Lewis acids, such as, e.g., $AlCl_3$, $FeBr_3$ or Fe, at temperatures between 30° and 150°, expediently between 50° and 150° in an inert solvent, such as, e.g., hydrocarbons, THF or carbon tetrachloride, with the compound of the formula I to be derivatized.

The compounds of formula I can possess one or more centers of asymmetry. When prepared, they can therefore be obtained as racemates or else in the optically active form if optically active starting materials are used. When synthesized, compounds possessing two or more centers of asymmetry are generally obtained as mixtures of racemates, from which the individual racemates can be isolated in the pure form, for example by recrystallization from inert solvents. If desired, the racemates obtained can be mechanically or chemically resolved into their optical antipodes by methods known per se. Preferably, diastereoisomers are formed from the racemate by reaction with an optically active resolving agent. Examples of suitable resolving agents are optically active acids such as the D and L forms of tartaric acid, dibenzoyltartaric acid, diacetyltartaric acid, camphorsulphonic acids, mandelic acid, malic acid or lactic acid. The different forms of the diastereoisomers can be resolved in a manner known per se, e.g., by fractional crystallization, and the optically active compounds of formula I can be liberated from the diastereoisomers in a manner known per se.

A base of formula I can be converted with an acid into the corresponding acid addition salt. Acids which produce biocompatible salts are suitable for this reaction. Thus, it is possible to use inorganic acids, e.g., sulphuric acid, hydrohalic acids such as hydrochloric acid or hydrobromic acid, phosphoric acids such as orthophosphoric acid, nitric acid and sulphamic acid, as well as organic acids, i.e.,specifically aliphatic, alicyclic, araliphatic, aromatic or heterocyclic monobasic or polybasic carboxylic, sulphonic or sulphuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulphonic or ethanesulphonic acid, ethanedisulphonic acid, 2-hydroxyethanesulphonic acid, benzenesulphonic acid, p-toluenesulphonic acid, naphthalenemonosulphonic and naphthalenedisulphonic acids and laurylsulphuric acid.

If desired, the free bases of formula I can be liberated from their salts by treatment with strong bases such as sodium or potassium hydroxide or sodium or potassium carbonate provided there are no other acid groups in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of formula I and their biocompatible salts for the manufacture of pharmaceutical preparations, especially by a non-chemical route. For this purpose, they can be converted into a suitable dosage form together with at least one excipient or adjunct and, if appropriate, in combination with one or more additional active ingredients.

The invention further relates to compositions, especially pharmaceutical preparations, containing at least one compound of formula I and/or one of their biocompatible salts. These preparations can be used as drugs in human or veterinary medicine. Possible excipients are organic or inorganic substances which are suitable for enteral (e.g., oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum Jelly. Tablets, coated tablets, capsules, syrups, Juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used, e.g., to manufacture injectable preparations.

The preparations indicated can be sterilized and/or can contain adjuncts such as lubricants, preservatives, stabilizers and/or wetting agents, emulsifiers, salts for influencing the osmotic pressure, buffer substances, colorants, taste correctors and/or flavorings. If desired, they can also contain one or more additional active ingredients, e.g., one or more vitamins.

The compounds of formula I and their biocompatible salts can be used for the therapeutic treatment of the human or animal body and for controlling diseases. They can be used for treating disorders of the central nervous system, such as tension, depressions and/or psychoses, and side-effects in the treatment of hypertension (e.g., with α-methyldopa). The compounds can also be used in endocrinology and gynaecology, e.g., for the therapeutic treatment of acromegaly, hypogonadism, secondary amenorrhoea, premenstrual syndrome and undesired puerperal lactation, and also for the prophylaxis and therapy of cerebral disorders (e.g., migraine), especially in geriatrics in a manner similar to certain ergot alkaloids and for controlling the sequelae of cerebral infarction (*Apoplexia cerebri*), such as stroke and cerebral ischaemia.

In these treatments, the substances of the invention are normally administered analogously to known, commercially available preparations (e.g., bromocriptine, dihydroergocornin), preferably in dosages of about 0.2 to 500 mg, especially of between 0.2 and 50 mg per dosage unit. The daily dosage is preferably about 0.001 to 10 mg/kg of body weight. The low dosages (abut 0.2 to 1 mg per dosage unit; about 0.001 to 0.005 mg/kg of body weight) are particularly suitable for use as antimigraine preparations; dosages of about 10 to 50 mg per dosage unit are preferred for the other indications. However, the particular dose for each individual patient depends on a very wide variety of factors, for example the activity of the particular compound used, age, body weight, general state of health, sex, diet, time and method of administration, rate of excretion, drug combination and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all. applications, patents and publications cited above, and of corresponding German application P 41 01 686.6, are hereby incorporated by reference.

EXAMPLES

In the following Examples, "working-up in conventional manner" means: Water is added if necessary, extraction is carried out with methylene chloride, the organic phase is separated off, dried over sodium sulphate and filtered, the filtrate is evaporated and the residue is purified by chromatography on silica gel and/or by crystallization. Temperatures are given in °C. Rf values were obtained by thin layer chromatography on silica gel.

Example 1

A solution of 2.6 g of 3-(4-chlorobutyl)-5-indolylurea [obtainable by reacting 5-nitroindole with 4-chlorobutyryl chloride to give 3-(4-chlorobutyryl)-5nitroindole, reduction with diborane to give 3-(4-chlorobutyl)-5-nitroindole hydrogenation to 3-(4-chlorobutyl)-5-aminoindole and reaction with KCNO] and 16.3 g of 1-phenylpiperazine in ("A") in 200 ml of acetonitrile is stirred for 12 hours at 20° and worked up in a conventional manner to give 3-[4-(4-phenylpiperazino)butyl]-5-indolylurea, hydrochloride, m.p. 207° (dec.).

The following are obtained analogously:

from 3-(4-chlorobutyl)-5-cyanoindole and "A" 3-[4-(4-phenylpiperazino)butyl]-5-cyanoindole, hydrochloride, m.p. 225°–227°;

from 3-(4-bromobutyl)indole-5-carboxamide and "A" 3-[4-(4-phenylpiperazino)butyl]indole-5-carboxamide, hydrate, hydrochloride, $R_f$0.45 (dichloromethane: methanol 20:1);

from 31(4-chlorobutyl)-5-hydroxymethylindole and "A" 3-[4-(4-phenylpiperazino)butyl]-5-hydroxymethylindole, m.p. 157°–158°;

from methyl 3-(4-bromobutyl)indole-5-carboxylate and "A" methyl 3-[4-(4-phenylpiperazino)butyl]indole-5-carboxylate, m.p. 126°–128°;

from 3-(4-chlorobutyl)indole-5-carboxylic acid and "A" 3-[4-(4-phenylpiperazino)butyl]indole-5-carboxylic acid, hydrochloride, m.p. 305°–307°;

from 3-(4-bromobutyl)indole-5-carboxylic acid morpholide and "A" 3-[4-(4-phenylpiperazino)butyl ]indole-5-carboxylic acid morpholide;

from 3-[4-chlorobutyl]indole-5-carboxylic acid piperidide and "A" 3-[4-(4-phenylpiperazino)butyl]indole-5-carboxylic acid piperidide;

from 3-(4-bromobutyl)indole-5-carboxylic acid 4-piperidinopiperidide and "A" 3-[4-(4-phenylpiperazino)butyl]indole-5-carboxylic acid 4-piperidinopiperidide;

from 3-(4-chlorobutyl)indole-5-carboxylic acid 4-morpholinopiperidide and "A" 3-[4-(4-phenylpiperazino)butyl]indole-5-carboxylic acid 4morpholinopiperidide;

from 3-(4-chlorobutyl)indole-5-carboxylic acid 4-p-chlorophenylpiperidide and "A" 3-[4-(4-phenylpiperazino) butyl]indole-5-carboxylic acid 4-p-chlorophenylpiperidide;

from 3-(4-chlorobutyl)indole-5-carboxylic acid 4-N,N-dimethylaminopiperidide and "A" 3-[4-(4-phenylpiperazino)butyl]indole-5-carboxylic acid 4 -N,N-dimethylaminopiperidide;

from 3-(4-bromobutyl)indole-5-carboxylic acid p-fluoroanilide and "A" 3-[4-(4-phenylpiperazino)-butyl]indole-5-carboxylic acid p-fluoroanilide;

from 3-(4-chlorobutyl)indole-5-carboxylic acid N-benzylamide and "A" 3-[4-(4-phenylpiperazino)butyl]indole-5-carboxylic acid N-benzylamide;

from 3-(4-bromobutyl)indole-5-carboxylic acid pyrrolidide and "A" 3-[4-(4-phenylpiperazino)butyl]indole-5-carboxylic acid pyrrolidide;

from 3-(4-chlorobutyl)indole-5-carboxylic acid 4-methylpiperazide and "A" 3-[4-(4-phenylpiperazino)butyl]indole-5-carboxylic acid 4-methylpiperazide;

from 3-(4-chlorobutyl)indole-5-carboxylic acid 4-N-(2-acetoxyethyl)amide and "A" 3-[4-(4-phenylpiperazino)butyl]indole-5-carboxylic acid 4-N-(2-acetoxyethyl)amide.

Example 2

By reaction of methyl 3-(4-bromobutyl)indole-5-carboxylate with 1-(o-methoxyphenyl)piperazine "B" analogously to Example 1, methyl 3-[4-(4-o-methoxyphenylpiperazino)butyl]indole-5-carboxylate is obtained; hydrate, hydrochloride, m.p. 195°–196°.

The following are obtained analogously
from 3-(4-chlorobutyl)indole-5-carboxylic acid and "B" 3-[4-(4-o-methoxyphenylpiperazino)butyl]indole-5-carboxylic acid, dihydrate, hydrochloride, m.p. 202°–204°;

from 3-(4-chlorobutyl) indole-5-carboxamide and "B" 3-[4-(4-o-methoxyphenylpiperazino)butyl]indole-5-carboxamide, hydrate, hydrochloride, m.p. 157°;

from 3-(4-chlorobutyl)indolylurea and "B" 3-[4-(4-o-methoxyphenylpiperazino)butyl]indole-5-indolylurea, hydrochloride, m.p. 130° (dec.);

from 3-(4-chlorobutyl) indole-5-carboxylic acid morpholide and "B" 3-[4-(4-o-methoxyphenylpiperazino)butyl]indole-5-carboxylic acid morpholide;

from 3-(4-chlorobutyl)indole-5-carboxylic acid anilide and "B" 3-[4-(4-o-methoxyphenylpiperazino)butyl]indole-5-carboxylic acid anilide;

from 3-(4-bromobutyl)-5-cyanoindole and "B" 3-[4-(4-o-methoxyphenylpiperazino)butyl]-5cyanoindole;

from 3-(4-chlorobutyl)indole-5-carboxylic acid N-methylpiperazide and 1-phenylpiperazine 3-[4-(4-phenylpiperazino)butyl]indole-5-carboxylic acid N-methylpiperazide;

from 3-(4-chlorobutyl)indole-5-carboxylic acid N-p-methoxyphenylpiperazide and 1-phenylpiperazine 3-[4-(4-phenylpiperazino)butyl]indole-5-carboxylic acid N-p-methoxyphenylpiperazide;

from 3-(4-chlorobutyl)indole-5-carboxylic acid 3-ketopiperazide and 1-phenylpiperazine 3-[4-(4-phenylpiperazino)butyl]indole-5-carboxylic acid 3-ketopiperazide;

from 3-(4-chlorobutyl)indole-5-carboxylic acid N-2-pyrimidinylpiperazide and 1-phenylpiperazine 3-[4-(4-phenylpiperazino)butyl]indole-5-carboxylic acid N-2-pyrimidinylpiperazide;

from 3-(4-chlorobutyl)indole-5-carboxylic acid N-formylpiperazide and 1-phenylpiperazine 3-[4-(4-phenylpiperazino)butyl]indole-5-carboxylic acid N-formylpiperazide;

from 3-(4-chlorobutyl)indole-5-carboxylic acid 4-ethoxycarbonylpiperidide and 1-phenylpiperazine 3-[4-(4-phenylpiperazino)butyl]indole-5-carboxylic acid 4-ethoxycarbonylpiperidide;

from 3-(4-chlorobutyl)indole-5-carboxylic acid 1,2,3,6-tetrahydropyridide and 1-phenylpiperazine 3-[4-(4-phenylpiperazino)butyl]indole-5-carboxylic acid 1,2,3,6-tetrahydropyridide.

Example 3

A mixture of 2.87 g of 3-(4-aminobutyl)-5-indolylurea [obtainable from 5-indolylurea via 3-(4-chlorobutyryl)-5-indolylurea, 3-(4-chlorobutyl) -5-indolylurea and 3-(4-phthalimidobutyl)-5-indolylurea] and one equivalent of N,N-bis(2-chloroethyl)-o-cyanoaniline ("C") in 40 ml of acetone and 40 ml of water is boiled for 24 hours and worked up in a conventional manner. 3-[4-(4-o-Cyanophenylpiperazino)butyl]-5-indolylurea, hydrochloride, m.p. 164°–166° is obtained.

The following are obtained analogously
from 3-(4-aminobutyl)-5-cyanoindole and N,N-bis(2-chloroethyl)-p-methoxyaniline 3-[4-(4-p-methoxyphenylpiperazino)butyl]-5-cyanoindole, hydrochloride, m.p. 207° (dec.);

from 3-(4-aminobutyl) -5-cyanoindole and "C" 3-[4-(4-o-cyanophenylpiperazino)butyl]-5-cyanoindole;

from 3-(4-aminobutyl) indole-5-carboxamide and N,N-bis(2-chloroethyl)-p-methoxyaniline 3-[4-(4-p-methoxyphenylpiperazino)butyl]indole-5-carboxamide, hydrochloride, m.p. 217° (dec.).

Example 4

A solution of 3.5 g of 3-[4-(4-p-methoxyphenylpiperazino)butyl]-5-aminoindole ["D"; obtainable by reduction of the corresponding 5-nitroindole] in 35 ml of THF is treated with a solution of 0.9 g of acetyl chloride in 10 ml of THF, and the mixture is stirred for 2 hours at 50°, evaporated and worked up in a conventional manner. 3-[4-(4-p-Methoxyphenylpiperazino)butyl]-5-acetamidoindole, hydrochloride, m.p. 240° (dec.) is obtained.

The following are obtained analogously
from methanesulphonyl chloride and "D" 3-[4-(4-p-methoxyphenylpiperazino)butyl]-5-methanesulphonamidoindole, hydrochloride, m.p. 208° (dec.);

from N,N-dimethylcarbamoyl chloride and "D" 3-[4-(4-p-methoxyphenylpiperazino)butyl]-5-N,N-dimethylureidoindole, hydrochloride, m.p. 187° (dec.);

from N,N-diethylcarbamoyl chloride and "D" 3-[4-(4-p-methoxyphenylpiperazino)butyl]-5-N,N-diethylureidoindole, hydrochloride, m.p. 145° (dec.);

from benzoyl chloride and "D" 3-[4-(4-p-methoxyphenylpiperazino)butyl]-5-benzamidoindole.

Example 5

A solution of 3.74 g of 3-[4-(4-phenylpiperazino)butyl]indole-5-carboxylic acid in 500 ml of DMF is treated with 1.01 g of N-methylmorpholine. A solution of one equivalent of tert-butylamine in 5 ml of DMF, 1.35 g of 1-hydroxybenzotriazole and a solution of 1.92 g of N-(3-dimethylaminopropyl-N'-ethylcarbodiimide hydrochloride in 20 ml of DMF are added with stirring. The mixture is stirred for 16 hours at 20° and the filtrate is evaporated. After working up in a conventional manner, 3-[4-(4-phenylpiperazino)butyl]indole-5-carboxylic acid N-tert-butylamide is obtained.

The following are obtained analogously
from 3-[4-(4-p-methoxyphenylpiperazino)butyl]indole-5-carboxylic acid and tert-butylamine 3-[4-(4-p-methoxyphenylpiperazino)butyl]indole-5-carboxylic acid N-tert-butylamide;

from 3-[4-(4-p-methoxyphenylpiperazino)butyl]indole-5-carboxylic acid and morpholine 3-[4-(4-p-methoxyphenylpiperazino)butyl]indole-5-carboxylic acid morpholide, m.p. 112°–116° ;

from 3-[4-(4-p-methoxyphenylpiperazino)butyl]indole-5-carboxylic acid and 4-piperidinopiperidine 3-[4-(4-p-methoxyphenylpiperazino)butyl]indole-5-carboxylic acid 4-piperidinopiperidide, hydrate, m.p. 116°–124°;

from 3-[4-(4-p-methoxyphenylpiperazino)butyl]indole-5-carboxylic acid and 2,6-dimethylmorpholine 3-[4-(4-p-methoxyphenylpiperazino)butyl]indole-5-carboxylic acid 2,6-dimethylmorpholide, hydrate, m.p. 115°–120°.

Example 6

A mixture of 4.05 g of 3-[4-(4-p-methoxyphenylpiperazino)butyl]-5-cyanoindole, 3.5 g of pyridine hydrochloride and 80 ml of pyridine is boiled for 3 hours. It is cooled, evaporated and worked up in a conventional manner, and 3-[4-(4-p-hydroxyphenylpiperazino)butyl]-5-cyanoindole is obtained.

Example 7

A suspension of 3.75 g o f 3-[4-(4-phenylpiperazino)butyl]-5-nitroindole in 45 ml of concentrated hydrochloric acid and 30 ml of ethanol is treated with 9.3 g of SnCl$_2$ with stirring and then boiled for 0.5 hour. The mixture is -poured onto ice and worked up in a conventional manner, and 3-[4-(4-phenylpiperazino)butyl ]-5aminoindole, R$_f$=0.45 (dichloromethane: methanol 20:1) is obtained.

The following is obtained analogously from 3-[4-(4-p-methoxyphenylpiperazino)butyl]-5-nitroindole by reduction
3-[4-(4-p-methoxyphenylpiperazino)butyl]-5aminoindole.

Example 8

A mixture of 30.6 g of 3-[4-(4-m-methoxyphenylpiperazino)butyl]-5-cyanoindole, 27.1 g of NaOH, 520 ml of water and 420 ml of diethylene glycol monoethyl ether is stirred for 3 hours at a bath temperature of 140°. It is cooled and worked up in a conventional manner, and 3-[4-(4-m-methoxyphenylpiperazino)butyl]indole-5-carboxamide is obtained.

The following are obtained analogously by partial hydrolysis of the corresponding nitriles:

3-[4-(4-o-methoxyphenylpiperazino)butyl]indole-5-carboxamide;

3-[4-(4-phenylpiperazino)butyl]indole-5-carboxyamide;

3-[4-(4-methoxyphenylpiperazino)butyl]indole-5-carboxamide, m.p. 217° (dec.);

3-[4-(4-o-fluorophenylpiperazino)butyl]indole-5-carboxamide;

3-[4-(4-m-fluorophenylpiperazino)butyl]indole-5-carboxamide;

3-[4-(4-p-fluorophenylpiperazino)butyl]indole-5-carboxamide;

3-[4-(4-p-trifluoromethylphenylpiperazino)butyl]indole-5-carboxamide.

Example 9

Starting from 3-[4-(4-p-methoxyphenylpiperazino)butyl]-5-cyanoindole analogously to Example 8, boiling for 16 hours and then working up in a conventional manner gives 3-[4-(4-p-methoxyphenylpiperazino)butyl]indole-5-carboxylic acid, dihydrate, hydrochloride, m.p. 268°–270° (dec.).

The following are obtained analogously from 3-[4-(4-m-methoxyphenylpiperazino)butyl]-5-cyanoindole 3-[4-(4-m-methoxyphenylpiperazino)butyl]indole-5-carboxylic acid, m.p. 146°–148°;

from 3-[4-(4-o-fluorophenylpiperazino)butyl]-5-cyanoindole 3-[4-(4-m-fluorophenylpiperazino)butyl]indole-5-carboxylic acid, m.p. 281°–283° (dec.);

from 3-[4-(4-m-fluorophenylpiperazino)butyl]-5-cyanoindole 3-[4-(4-m-fluorophenylpiperazino)butyl]indole-5-carboxylic acid;

from 3-[4-(4-p-fluorophenylpiperazino)butyl]-5-cyanoindole 3-[4-(4-p-flUorophenylpiperazino)butyl]indole-5-carboxylic acid, m.p. 264°–266° (dec.);

from 3-[4-(4-o-methylphenylpiperazino)butyl]-5-cyanoindole 3-[4-(4-o-methylphenylpiperazino)butyl]indole-5-carboxylic acid;

from 3-[4-(4-m-methylphenylpiperazino)butyl]-5-cyanoindole 3-[4-(4-m-methylphenylpiperazino)butyl]indole-5-carboxylic acid from 3-[4-(4-p-methylphenylpiperazino)butyl]-5-cyanoindole 3-[4-(4-p-methylphenylpiperazino)butyl]indole-5-carboxylic acid;

from3-[4-(4-o-trifluoromethylphenylpiperazino)butyl]-5-cyanoindole 3-[4-(4-o-trifluoromethylphenylpiperazino)butyl]indole-5-carboxylic acid;

from 3-[4-(4-m-trifluoromethylphenylpiperazino)butyl ]-5-cyanoindole 3-[4-(4-m-trifluoromethylphenylpiperazino)butyl]indole-5-carboxylic acid, m.p. 217°–219°;

from 3-[4-(4-p-trifluoromethylphenylpiperazino)butyl ]-5-cyanoindole 3-[4-(4-p-trifluoromethylphenylpiperazino)butyl]indole-5-carboxylic acid;

from 3-[4-(4-(2,4-dimethoxyphenyl)piperazino)butyl]-5-cyanodindole 3-[4-(4-(2,4-dimethoxyphenyl)piperazino)butyl]indole-5-carboxylic acid, m.p. 257°–258°;

from 3-[4-(4-(2,4-difluorophenyl)piperazino)butyl]-5-cyanoindole 3-[4-(4-(2,4-difluorophenyl) piperazino)butyl]indole-5-carboxylic acid.

Example 10

A solution of 4.3 g of methyl 3-[4-(4-phenylpiperazino)butyl]indole-5-carboxylate in 40 ml of THF is added dropwise with stirring in an N$_2$ atmosphere at 20° to a suspension of 0.6 g of lithium aluminium hydride in 20 ml of THF. The mixture is stirred for 1 hour at 20°, decomposed with dilute sodium hydroxide solution and filtered, the filtrate is worked up in a customary manner and 3-[4-(4-phenylpiperazino)butyl]-5-hydroxymethylindole, m.p. 157°–158°, is obtained.

The following is obtained analogously from 3-[4-(4-p-methoxyphenyl-piperazino)butyl]indole-5-carboxylate 3-[4-(4-p-methoxyphenyl-piperazino)butyl]-5-hydroxymethylindole, m.p. 162°–164°.

Example 11

HCl gas is passed into a boiling solution of 4 g of 3-[4-(4-m-methoxyphenylpiperazino)butyl]indole-5-carboxylic acid in 50 mi of absolute methanol for 2 hours. The mixture is then boiled for a further hour and worked up in a conventional manner, and methyl 3-[4-(4-m-methoxyphenylpiperazino)butyl]indole-5-carboxylate, m.p. 176°–177°, is obtained.

The following are obtained analogously by esterification with methanol from 3-[4-(4-o-methoxyphenylpiperazino)butyl]indole-5-carboxylic acid methyl 3-[4-(4-o-methoxyphenylpiperazino)butyl]indole-5-carboxylate from 3-[4-(4-p-methoxyphenylpiperazino)butyl]indole-5-carboxylic acid methyl 3-[4-(4-p-methoxyphenylpiperazino)butyl]indole-5-carboxylate, m.p. 236°–238° (dec.);

from 3-[4-(4-o-fluorophenylpiperazino)butyl]indole-5-carboxylic acid methyl 3-[4-(4-o-fluorophenylpiperazino)butyl]indole-5-carboxylate, m.p. 214°–217°;

from 3-[4-(4-m-fluorophenylpiperazino)butyl]indole-5-carboxylic acid methyl 3-[4-(4-m-fluorophenylpiperazino)butyl]indole-5-carboxylate;

from 3-[4-(4-p-fluorophenylpiperazino)butyl]indole-5-carboxylic acid methyl 3-[4-(4-p-fluorophenylpiperazino)butyl]indole-5-carboxylate, m.p. 121°–124°;

from 3-[4-(4-p-trifluoromethylphenylpiperazino)butyl]indole-5-carboxylic acid methyl 3-[4-(4-p-trifluoromethylphenylpiperazino)butyl]indole-5-carboxylate;

from 3-[4-(4-m-trifluoromethylphenylpiperazino)butyl]indole-5-carboxylic acid methyl 3-[4-(4-m-trifluoromethylphenylpiperazino)butyl]indole-5-carboxylate, m. p. 142°–144° from 3-[4-(4-m-methylphenylpiperazino)butyl]indole-5-carboxylic acid methyl 3-[4-(4-m-methylphenylpiperazino)butyl]indole-5-carboxylate, m.p. 158°–162°;

from 3-[4-(4-o-cyanophenylpiperazino)butyl]indole-5-carboxylic acid methyl 3-[4-(4-o-cyanophenylpiperazino)butyl]indole-5-carboxylate, m.p. 230°–232°;

from 3-[4-(4-p-cyanophenylpiperazino)butyl]indole-5-carboxylic acid methyl 3-[4-(4-p-cyanophenylpiperazino)butyl]indole-5-carboxylate;

from 3-[4-(4-m-cyanophenylpiperazino)butyl]indole-5-carboxylic acid methyl 3-[4-(4-m-cyanophenylpiperazino)butyl]indole-5-carboxylate;

from 3-[4-(4-(2,4-dimethoxyphenyl)piperazino)butyl]indole-5-carboxylic acid methyl 3-[4-(4-(2,4-dimethoxyphenyl)piperazino)butyl]indole-5-carboxylate, m.p. 190°–192°.

Example 12

4.8 g of methyl 3-[4-(4-o-methoxyphenylpiperazino)butyl]indole-5-carboxylate are boiled for ½ an hour with 20 ml of water and 100 ml of 2N ethanolic KOH and worked up in a conventional manner, and 3-[4-(4-omethoxyphenylpiperazino)butyl]indole-5-carboxylic acid is obtained.

Example 13

By reaction of 17.8 g of 3-(4-chlorobutyl)-5-indolylurea with one equivalent of 1-(o-cyanophenyl)-piperazine analogously to Example 1, 3-[4-(4-o-cyanophenylpiperazino)butyl]-5-indolylurea, m.p. 220°–222°, is obtained.

Example 14

By reaction of 9.6 g of 3-(4-chlorobutyl)-5-indolylurea with one equivalent of 1-(p-methoxyphenyl)piperazine analogously to Example 1, 3-[4-(4-p-methoxyphenyl)piperazino)butyl]-5-indolylurea, m.p. 225° (dec.), is obtained.

Example 15

A solution of 10.8 g of 3-[4-(N,N-bis(2-chloroethyl)amino)butyl]-5-cyanoindole ("E") [obtainable by reaction of 3-(4-chlorobutyl)-5-cyanoindole with N,N-bis(2-chloroethyl)amine] and one equivalent of p-methoxyaniline in 200 ml of acetonitrile is stirred for 12 hours at room temperature and worked up in a conventional manner, and 3-[4-(4-p-methoxyphenylpiperazino)-butyl]-5-cyanoindole, m.p. 207° (dec.), is obtained.

The following are obtained analogously by reaction of "E" with o-methoxyaniline 3 -[4-(4-o-methoxyphenylpiperazino)butyl]-5-cyanoindole;
of "E" with 2,4-dimethylaniline 3 -[4-(4-(2,4-dimethylphenylpiperazino)butyl]-5-cyanoindole;
of "E" with p-fluoroaniline 3 -[4-(4-p-fluorophenylpiperazino)butyl]-5-cyanoindole;
of "E" with o-fluoroaniline 3-[4-(4-o- fluorophenylpiperazino)butyl]-5-cyanoindole;
of "E" with m-methoxyaniline 3-[4-(4-m-methoxyphenylpiperazino)butyl]-5-cyanoindole;
of "E" with p-trifluoromethylaniline 3-[4-(4-p-trifluoromethylphenylpiperazino)butyl ]-5cyanoindole;
of "E" with 2,4-dimethoxyaniline 3-[4-(4- (2,4-dimethoxyphenyl)piperazino)butyl]-5-cyanoindole.

Example 16

A mixture of 4 g of 3-[4-(4-p-methoxyphenylpiperazino)butyl]indole-5-carboxylic acid, 3.2 g of pyridine hydrochloride and 80 ml of pyridine is boiled for 3 hours. It is cooled, evaporated and worked up in a conventional manner, and 3-[4-(4-p-hydroxyphenylpiperazino)butyl]indole-5-carboxylic acid is obtained.

The following is obtained analogously
from 3-[4-(4-(2,4-dimethoxyphenyl)piperazino)butyl]-5-cyanoindole 3-[4-(4-(2,4-dihydroxyphenyl)piperazino)butyl]-5-cyanoindole.

Example 17

4.6 g of 1-benzenesulphonyl-3-[4-(4-phenylpiperazino)butyl]-5-1indolylurea [obtainable from 1-benzenesulphonyl-3-(4-chlorobutyl)-5-indolylurea and 1-phenylpiperazine] are boiled with 1.5 g of KOH in aqueous ethanol solution for 16 hours and worked up in a conventional manner, and 3-[4-(4-phenylpiperazino)butyl]-5indolylurea, hydrochloride, m.p. 207° (dec.), is obtained.

Example 18

2,4 g of 3-[4-(4-p-benzyloxyphenylpiperazino)butyl]indole-5-carboxamide are dissolved in 30 ml of toluene and treated at room temperature for 1 hour with $H_2$ gas (p=1 atm) under the catalytic action of 200 mg of Pd/C (Pd content 1%), The reaction mixture is then filtered and 3-[4-(4-p-hydroxyphenylpiperazino)butyl]indole-5-carboxamide is obtained by conventional working up.

The following Examples relate to pharmaceutical preparations containing amines of formula I or their acid addition salts:

Example 19

Analogously to Example 1 one obtains by reaction of 1-(4-methoxyphenyl)-piperazine
with 3-(4-chlorobutyl)-indole-5-carboxylic acid-4-(p-methoxyphenyl)-piperazide: 3-[4-(4-(4-methoxyphenyl)-piperazino)-butyl]-indole-5-carboxylic acid -4-(p-methoxyphenyl)-piperazide, m.p. 146°–148°;
with 3-(4-chlorobutyl)-indole-5-carboxylic acid-4-methylpiperazide: 3-[4-(4-(4-methoxyphenyl)-piperazino)-butyl]-indole-5-carboxylic acid-4-methylpiperazide, m.p. 92°–94°;
with 3-(4-Chlorobutyl)-indole-5-carboxylic acid-(N-methyl-4-pyridine)-amide: 3-[4-(4-(4-methoxyphenyl)-piperazino)-butyl]-indole-5-carboxylic acid-(N-methyl-4-pyridine)-amide, m.p. 180°–182°;

with 3-(4-chlorobutyl)-indole-5-carboxylic acid-3-oxo-piperazide: 3-[4-(4-(4-methoxyphenyl)-piperazino)-butyl]-indole-5-carboxylic acid-3-oxo-piperazide, m,p, 162°–164°;

with 3-(4-chlorobutyl)-indole-5-carboxylic acid-4-formylpiperazide: 3-[4-(4-(4-methoxyphenyl)-piperazino)-butyl]-indole-5-carboxylic acid-4-formyl-piperazide, m.p. 159°–162°;

with 3-(4-chlorobutyl)-indole-5-carboxylic acid-N-(2-methoxyethyl)-amide: 3-[4-(4-(4-methoxyphenyl)-piperazino)-butyl]-indole-5carboxylic acid-N-(2-methoxyethyl)-amide, m.p. 187°–190°;

with 3-(4-chlorobutyl)-indole-5-carboxylic acid-N-(2-piperidinoethyl)-amide: 3-[4-(4-(4 -methoxyphenyl)-piperazino)-butyl]-indole-5-carboxylic acid-N-(2-piperidino-ethyl)-amide, m.p. 219°–221°;

with 3-(4-chlorobutyl)-indole-5-carboxylic acid-N-(2-pyrrolidinoethyl)-amide: 3-[4-(4-(4-methoxyphenyl)-piperazino)-butyl]-indole-5-carboxylic acid-N-(2-pyrrolidino-ethyl)-amide. m.p. 180°–184°;

with 3-(4-chlorobutyl)-indole-5-carboxylic acid-N-(2-(N,N-diethylamino)-ethyl)-amide: 3-[4-(4-(4-methoxyphenyl)-piperazino)-butyl]-indole-5-carboxylic acid-N-(2-(N,N-diethylamino)-ethyl)-amide, m.p. 221°–225°;

with 3-(4-chlorobutyl)-indole-5-carboxylic acid-(4-dioxoethylene)-piperidide: 3-[4-(4-(4-methoxyphenyl-piperazino)-butyl]-indole-5carboxylic acid-(4-di-oxo-ethylene)-piperidide, m.p. 120°–131°.

Example 20

Analogously to Example 8 one obtains by partial hydrolysis of the corresponding nitriles:

3-[4-(4-(3,4-methylendioxy-phenyl) -piperazino)-butyl]-indole-5-carboxylic acid amide, m.p. 177°–179°;

3-[4-(4-(3,5-dichloro-4-methoxy-phenyl)-piperazino)-butyl]-indole-5-carboxylic acid amide, m.p. 115° (d);

3-[4-(4-(4-hydroxy-phenyl)-piperazino)-butyl]-indole-5-carboxylic acid amide, m.p. 141° (d);

3-[4-(4-(4-acetamido-phenyl)-piperazino)-butyl]-indole-5-carboxylic acid amide, m.p. 230° (d).

Example A: Tablets

A mixture of 1 kg of methyl 3-[4-(4-phenyl-piperazino)butyl]indole-5-carboxylate, 4 kg of lactose, 1.2 kg of potato starch, 0.2 kg of talc and 0.1 kg of magnesium stearate is compressed to tablets in conventional manner so that each tablet contains 10 mg of active ingredient.

Example B: Coated tablets

Tablets are formed by compression analogously to Example A and then covered in conventional manner with a coating of sucrose, potato starch, talc, tragacanth and colorant.

Example C: Capsules 2 kg of 3-[4-(4-phenylpiperazino)butyl]-5-indolylurea are filled into hard gelatin capsules conventional manner so that each capsule contains 20 mg of the active ingredient.

Example D: Ampoules

A solution of 1 kg of 3-[4-(4-phenylpiperazino)butyl]-5-indolylurea dihydrate in 60 l of double-distilled water is filtered under sterile conditions, filled into ampoules and lyophilized under sterile conditions and the ampoules are sealed under sterile conditions. Each ampoule contains 10 mg of active ingredient.

Tablets, coated tablets, capsules and ampoules containing one or more of the other active ingredients of formula I and/or their biocompatible acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indole compound of formula I

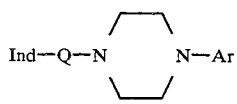

wherein

Ind is an indol-3-yl radical substituted in the 4-, 5-or 6-position by CO—R$^1$;

R$^1$ is NH$_2$;

Q is —(CH$_2$)$_4$—; and

AR is a phenyl radical substituted by a methylenedioxy group, or a physiological acceptable salt thereof.

2. A pharmaceutical composition comprising an effective amount of a compound according to claim 1 and a pharmaceutically acceptable carrier.

3. A pharmaceutical composition according to claim 2, wherein said compound is present in an amount of 0.2–500 mg.

4. A pharmaceutical composition according to claim 3, wherein said compound is present in an amount of 0.2–50 mg.

5. A method of treating tension, depression, psychosis, or side effects associated with the treatment of hypertension, comprising administering a compound according to claim 1.

6. A method of treating acromegaly, hypogonadism, secondary amenorrhoea, premenstrual syndrome or undesired puerperal lactation comprising administering a compound according to claim 1.

7. A method of treating migraines, comprising administering a compound according to claim 1.

8. A method according to claim 7, wherein said compound is administered in a daily dosage of 0.001–0.005 mg/kg of body weight.

9. A method of treating depression in a patient in need thereof, comprising administering an effective amount of a compound according to claim 1.

10. A method of treating hypertension in a patient in need thereof, comprising administering an effective amount of a compound according to claim 1.

11. An indole compound of formula I

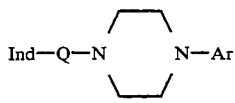

wherein
Ind is an indol-3-yl radical substituted in the 4-, 5-or 6-position by CO—R$^1$;
R$^1$ NH$_2$;

Q is —(CH$_2$)$_4$—, —(CH$_2$)$_5$—, or —(CH$_2$)$_6$; and
Ar is a phenyl radical substituted by a methylenedioxy group;
or a physiological acceptable salt thereof.

12. A method of treating depression in a patient in need thereof, comprising administering an effective amount of a compound according to claim 11.

13. A method of treating hypertension in a patient in need thereof, comprising administering an effective amount of a compound according to claim 11.

* * * * *